United States Patent [19]

Stern

[11] Patent Number: 4,687,257
[45] Date of Patent: Aug. 18, 1987

[54] METHOD OF MAKING BRUSHES, AND BRUSHES THUS MADE

[76] Inventor: Leif E. Stern, Fattershus, S-225 90 Lund, Sweden

[21] Appl. No.: 871,411

[22] PCT Filed: Oct. 1, 1985

[86] PCT No.: SE85/00379

§ 371 Date: May 29, 1986

§ 102(e) Date: May 29, 1986

[87] PCT Pub. No.: WO 86/01984

PCT Pub. Date: Apr. 10, 1986

[30] Foreign Application Priority Data

Oct. 1, 1984 [SE] Sweden .................... 8404885

[51] Int. Cl.$^4$ ............................................ A61C 15/00
[52] U.S. Cl. ................................ 300/21; 15/167 R; 132/89
[58] Field of Search ............... 15/159, 167, 190–193; 132/89, 93; 300/21; 425/174, 174.8

[56] References Cited

U.S. PATENT DOCUMENTS 3,939,520  2/1976  Axelsson .
4,008,727  2/1977  Thornton ........................ 132/89

FOREIGN PATENT DOCUMENTS 374999   4/1975  Sweden .
425141   9/1982  Sweden .
2024630A 1/1980  United Kingdom .

OTHER PUBLICATIONS

"Idea Exchange", Modern Plastics International, Jul. 1980, p. 17.

Primary Examiner—Timothy V. Eley
Attorney, Agent, or Firm—Schwartz, Jeffery, Schwaab, Mack, Blumenthal & Evans

[57] ABSTRACT

This invention relates to a method of making brushes for cleaning preferably bacteria-polluted surfaces, particularly the skin, gums or teeth, in which the body (1) of the brush shall be provided with a great many bristles (2) designed to collectively form a uniformly distributed bristle covering on the brush body (1) or parts thereof. To apply the bristles (2) to the brush body (1) in a very rapid and solid manner even though the body and the brush are very small, a surface (3) of polyamide material of the brush body (1) is supplied with a water-soluble organic acid (8) to dissolve the brush body surface (3) of polyamide material, whereupon bristles (2) of preferably polyamide material are attracted to the brush body (1) by electrostatic attraction so that those end portions (17) of each bristle which come in contact with the dissolved surface (3) of the brush body (1) are dissolved and caused to fuse with said surface to form a brush in which the body (1) and all bristles (2) are integrated into a unit. A brush product particularly suitable for dental care, which has been produced by this method, has a body (1) comprising an end portion (1a) devoid bristles to permit being grasped during brushing without coming in contact with the bristle-carrying parts of the body (1).

10 Claims, 6 Drawing Figures

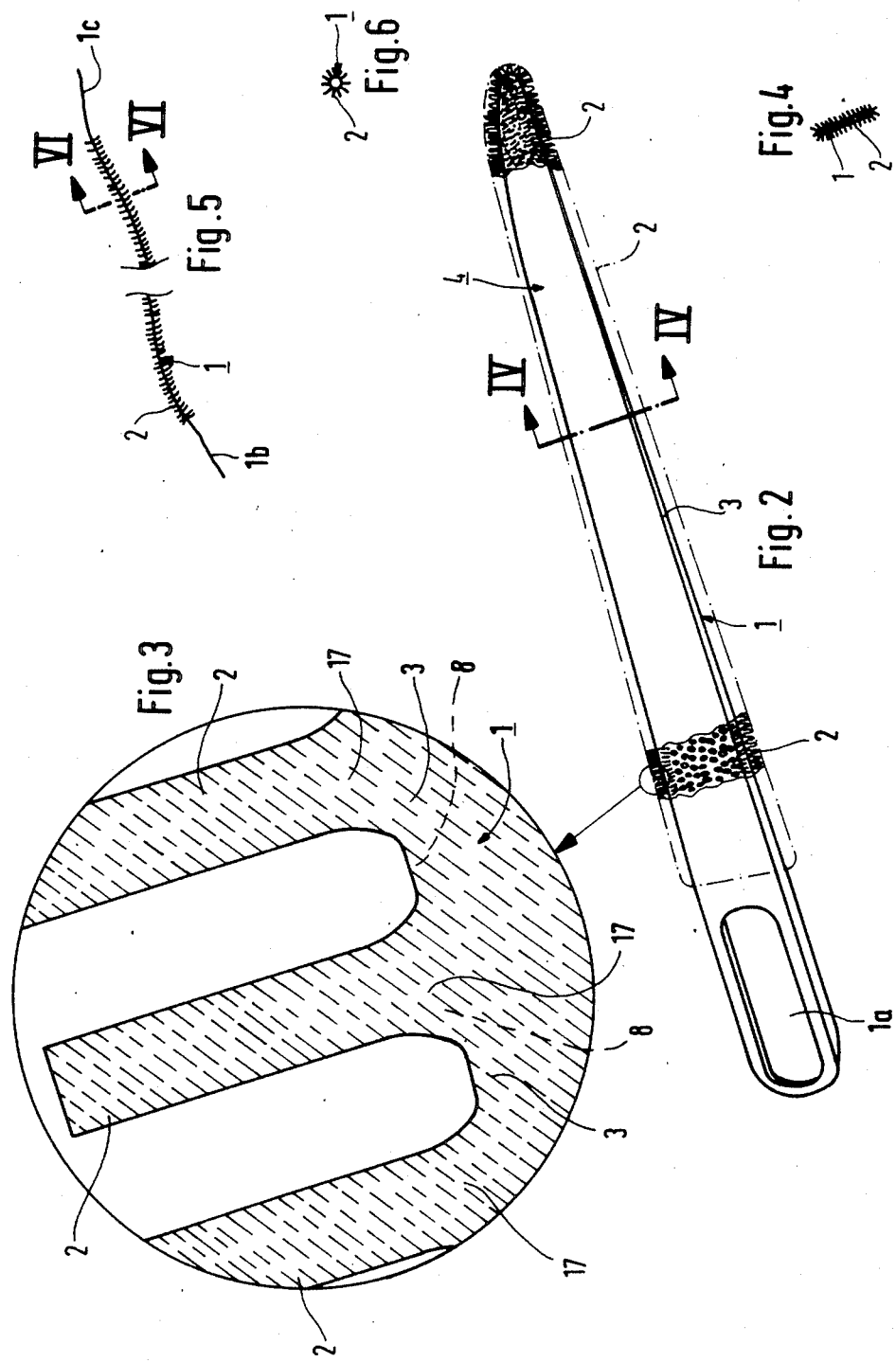

METHOD OF MAKING BRUSHES, AND BRUSHES THUS MADE

BACKGROUND OF THE INVENTION

1. Field of the Invention

This invention relates to a method of making brushes for cleaning preferably bacteria-polluted surfaces, particularly the skin, gums or teeth, in which the body of the brush shall be provided with a great many bristles designed to collectively form a uniformly distributed covering on the brush body or parts thereof. The invention also relates to brushes made by the novel method.

2. Related Art

In many cases, it has proved very difficult to apply the bristles of the brush to the brush body in a rational and besides durable manner. These problems are particularly serious where small brushes are concerned, which are designed for cleaning the skin, gums or teeth, because relatively small brush bodies and bristles are required for such brushes. Attempts to secure small bristles by gluing to small brush bodies have not been very successful.

SUMMARY OF THE INVENTION

The present invention aims at eliminating this problem and providing a novel method that permits applying the bristles in a very rapid and solid manner to the brush body even though the body and the bristles are very small. This aim is achieved by the invention substantially in that the novel inventive method comprises the features defined by appended claim 1.

Furthermore, the invention has the purpose of providing an advantageous brush made by the method according to the invention.

BRIEF DESCRIPTION OF THE DRAWINGS

The invention is elucidated more in detail below with reference to the accompanying drawings in which:

FIG. 2 illustrates a finished brush made by the method of the invention;

FIG. 3 illustrates an enlarged section of the brush shown in FIG. 2;

FIG. 4 illustrates a section on line IV—IV in FIG. 2;

FIG. 5 illustrates a brush of alternative design; and

FIG. 6 illustrates a section on line VI—VI in FIG. 5.

DETAILED DESCRIPTION OF THE PREFERRED EMBODIMENTS

Figure 1:
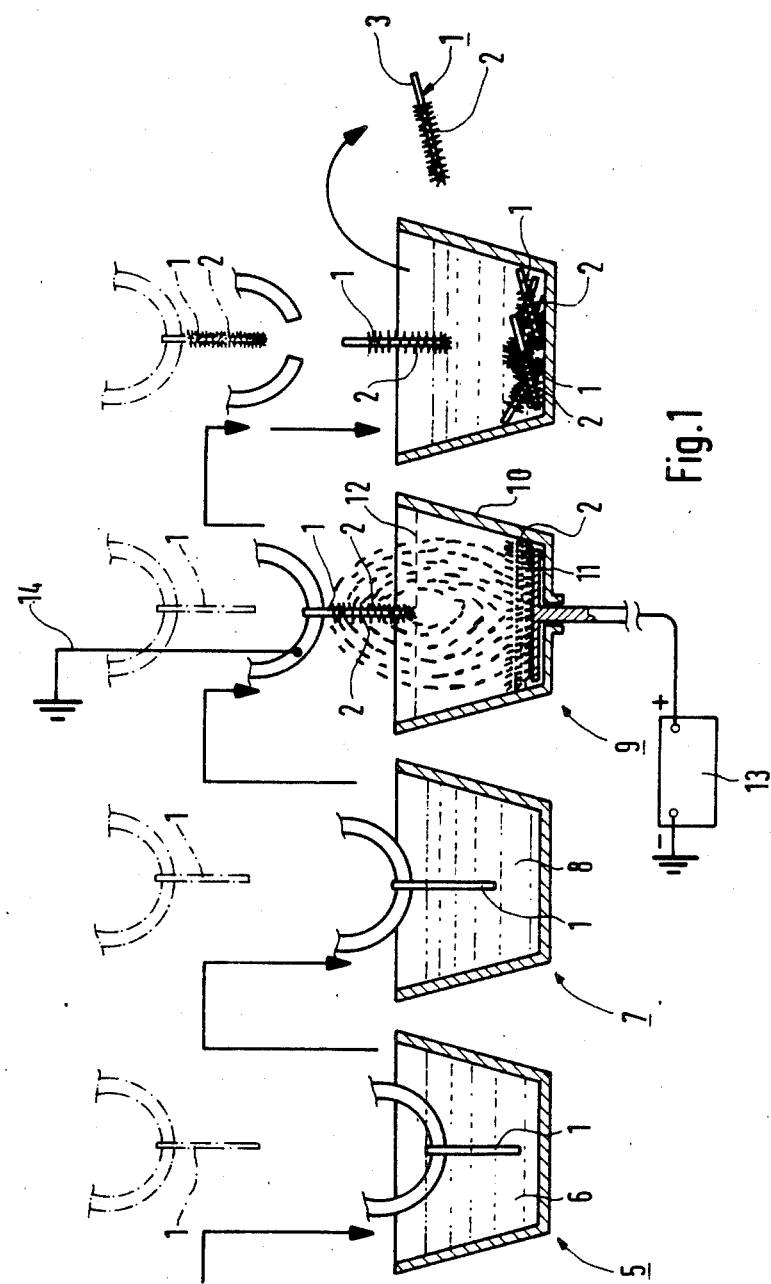
FIG. 1 diagrammatically illustrates the method of the invention.

The method of making a brush, which is illustrated in FIG. 1, serves to make a relatively small brush for brushing the gums and teeth. The brush comprises a body 1 and a great number of bristles 2. The body 1 to at least the major part consists of polyamide material or has a surface 3 of polyamide material, and bristles 2 of the brush also consist of polyamide material. In this instance, the body 1 suitably is 30–70 mm, preferably about 50 mm, long and at its widest part about 6 mm wide and at its thickest part about 2 mm thick. The body 1 has an elongated and tapering apex 4 which suitably constitutes the major part of the body 1. The bristles 2 of the brush are of a length of approximately 0.5–2 mm (the bristles may be of equal length or of different lengths) and the thickness of the bristles 2 is essentially less than the length thereof. These small bristles 2 are designed to be applied to the relatively small brush body 1 in a rational and extremely solid manner.

FIG. 1 diagrammatically illustrates how the method of the invention is carried out. If necessary, the brush body 1 at station 5 is dipped into water 6 in its entire length for moistening of the entire body 1, thus making it possible for the surface 3 thereof to become current-conductible. The body 1 is then moved to station 7 where it is dipped into a water-soluble organic acid 8, preferably formic acid.

At station 7, only those parts of the body 1, that is its apex 4, to which bristles shall be applied, are submerged. The water-soluble organic acid causes the surface 3 of the brush body 1 to be dissolved. At the following station 9 the body 1 with the surface 3 in dissolved state is held over a container 10 with an electrode 11 at its bottom, a larger number of bristles 2 and a grid 12 at its top, having such a mesh width that the bristles 2 can pass therethrough. The bristles 2 consist of preferably the same polyamide material as the surface 3 of the brush body 1 (or possibly as the entire brush body), and the bristles lie in a fully loose state in the container 10.

The electrode 11 is connected to a current source 13 and the brush body 1 is disposed above the container 10 spaced a suitable distance from the electrode 11. With the body 1 in this position, the current-conductible surface 3 thereof is earthed via a holder, which keeps the body in position, and an earth connection 14 extending from said holder. On supply of current from the current source 13 to the electrode 11 there is generated an electric field between the electrode 11 and the current-conductible surface 3 of the brush body 1, whereby the bristles 2 are attracted to the body 1 simultaneously as said bristles 2 repel each other, being thus uniformly distributed over the surface 3 of the brush body 1. By reason of this electrostatic attraction of the bristles 2 they will orientate themselves so as to protrude straight outward from the brush body 1, making a substantially right angle with those parts of the brush body surface 3 to which they adhere.

As the end portions 17 of the bristles 2 contact the dissolved surface 3 of the brush body 1, said end portions 17 are dissolved by the action of the water-soluble organic acid 8 which is present on the dissolved surface 3 of the brush body. As a result, the dissolved brush body surface 3 and the end portions 17 of the bristles 2 are fused together and when the fused parts 3, 7 have solidified the bristles 2 will be fully integrated with the brush body 1, thus forming inseperable parts.

Of special advantage is that also the narrowest portions of the brush body apex 4 present fully integrated bristles 2, that if the bristles 2 are heavily anchored also to narrow parts of the brush body 1.

In addition to the finished brush product obtaining a solidly adhering bristle covering, it can also be given a bacteria-inhibiting effect because it is made of polyamide material and/or because it has been treated with a water-soluble organic acid of bacteria-inhibiting action.

The effect of the bristle application can be varied by varying the time and/or the effect of the electric charge of the bristles 2. Besides, during the bristle application procedure the distance of the brush body 1 to the bristles may be variable and/or the length of the attraction moment may be variable.

As only the surface 3 of the lower parts 4 (apex 4) of the brush body 1 has been exposed to water-soluble organic acid 8 while the surface of the upper parts 1a (a handle portion 1a) of the brush body 1 has not been exposed to said acid 8, only the surface 3 of the lower parts 4 and not that of the upper parts 1a of the brush body is fused, which implies that the bristles 2 only adhere to the lower parts 4 and not to the upper part 1a of the brush body. As a result, there is formed in a simple manner a handle portion 1a devoid of bristles on the brush body 1.

The brush body 1 having integrated bristles 2 thereon may be moved to a station 15 in which the finished brush products are washed in water 16 for removal of excess acid possibly remaining on the products. At the same time, loose bristles 2 may be removed from the products by flushing, shaking, rubbing, blowing or otherwise whereafter the products are ready for packaging and deliviery.

The invention is not restricted to the process described or the product described, but can be varied within the spirit and scope of the appended claims. Thus, water-soluble organic acids other than formic acid may be employed. The number and type of processing stations may vary, for instance the moistening of the brush body 1 may take place by spraying of the body instead of submerging it in water or other suitable liquid at station 5. A particular moistening operation may be dispensed with if the brush body 1 before the submerging thereof in organic acid has been stored or transported in so moist an environment that it has absorbed a sufficient quantity of moisture to make the surface of the brush body current-conducible.

The brush product described in the foregoing and illustrated in the drawings is small and specifically suited for dental care, and even though the dimensions indicated are specifically suited for a small brush product for such purposes, the dimensions indicated may be exceeded without making the product unusable for its purpose. The dimensions of the brush product may still vary essentially beyond those mentioned in the specification in case the brush product is to be used for other purposes, i.e. for care of the skin, for which purpose there are required brush products or larger dimensions than those mentioned.

In the brush embodiment illustrated in FIGS. 5 and 6 the brush body 1 consists of an elongated flexible thread of polyamide material and this thread is of substantially circular cross sectional area and intended for use as dental floss. When submerged in the organic acid 8 at station 7, the floss end portions 1b, 1c are not dipped into the acid 8 but only the floss segment intermediate the end portions 1b, 1c. This implies that the end portions 1b, 1c of the dental floss are not coated with bristles at station 9 but only the intermediate parts thereof. As a result, the dental floss will present a first end portion 1b or 1c by which it can be grasped during the cleaning operation, and a second end portion 1c or 1b which is adapted to serve as a dental floss apex for facilitating the penetration of the dental floss between the teeth. The body 1 in this case is of such rigidity that the dental floss substantially retains its shape at the introduction of the apex thereof between the teeth, while the other end portion devoid of bristles is grasped as a handle portion. The body 1, however, is not so rigid that it cannot be easily bent during the cleaning operation. By reason of the bristle covering, the bristle-coated part of the dental floss will be somewhat more rigid than the floss end portions 1b, 1c.

What is claimed is:

1. A method of making brushes for cleaning preferably bacteria-polluted surfaces, particularly the skin, gums or teeth, in which a body of the brush is provided with designed to collectively form a uniformly distributed bristle covering on the brush body or parts thereof, comprising the steps of: supplying a surface of polyamide material of the brush body with a water-soluble organic acid to dissolve the brush body surface of polyamide material, and attracting bristles of to the brush body by electrostatic attraction so that end portions of each bristle which come in contact with the dissolved surface of the brush body are dissolved and caused to fuse with said surface to form a brush in which the body and all bristles are integrated into a unit.

2. A method as claimed in claim 1, characterized in that the bristles are attracted by said electrostatic attraction to cause them to orientate in such a manner as to protrude substantially straight outwardly from the brush body and to be spaced substantially the same distances apart.

3. A method as claimed in claim 1, characterized in that the bristles are electrically charged and attracted to the brush body by imparting to the dissolved surface of the brush body electrically conducting properties and an electric polarity opposite to the electric charge of the bristles.

4. A method as claimed in claim 1, characterized in that the time for the electric charge of the bristles to bring about their attraction to the brush body is variable.

5. A method as claimed in claim 1, characterized in that the water-soluble organic acid is formic acid.

6. A method as claimed in claim 1 characterized in, only parts of the brush body are provided with bristles, and that the entire brush body is moistened to make the surface thereof electrically conductible, and whereupon only those parts which are provided with bristles are supplied with said water-soluble organic acid.

7. A method as claimed in claim 1, characterized in that excess water-soluble organic acid is caused to evaporate after the bristles on the brush body have fused with the surface of the brush body.

8. A method as claimed in claim 1, characterized in that the effect of the electric charge of the bristles to bring about their attraction to the brush body is variable.

9. A method as claimed in claim 1, characterized in that the distance of the brush body to the bristles during the attraction moment is variable.

10. A method as claimed in claim 1, characterized in that the length of the attraction moment is variable.

* * * * *